United States Patent
Ao et al.

(10) Patent No.: US 9,244,001 B2
(45) Date of Patent: Jan. 26, 2016

(54) COLORIMETER MEASUREMENT METHOD AND COLORIMETER FOR IMPLEMENTING THE METHOD

(71) Applicant: SHENZHEN CHINA STAR OPTOELECTRONICS TECHNOLOGY CO., LTD., Shenzhen, Guangdong (CN)

(72) Inventors: Xueli Ao, Shenzhen (CN); Weiwei Zhang, Shenzhen (CN); Jingming Wu, Shenzhen (CN); Rui Xu, Shenzhen (CN); Li Wang, Shenzhen (CN); Xiaobo He, Shenzhen (CN); Honghui Zhu, Shenzhen (CN)

(73) Assignee: SHENZHEN CHINA STAR OPTOELECTRONICS TECHNOLOGY CO., LTD., Shenzhen (CN)

( * ) Notice: Subject to any disclaimer, the term of this patent is extended or adjusted under 35 U.S.C. 154(b) by 42 days.

(21) Appl. No.: 14/359,578

(22) PCT Filed: Mar. 28, 2014

(86) PCT No.: PCT/CN2014/074281
§ 371 (c)(1),
(2) Date: May 20, 2014

(87) PCT Pub. No.: WO2015/131425
PCT Pub. Date: Sep. 11, 2015

(65) Prior Publication Data
US 2015/0276584 A1 Oct. 1, 2015

(30) Foreign Application Priority Data
Mar. 3, 2014 (CN) .............................. 201410075884

(51) Int. Cl.
*G01N 21/25* (2006.01)
*G01J 3/46* (2006.01)
*G01N 21/84* (2006.01)
*G01B 11/27* (2006.01)

(52) U.S. Cl.
CPC ............ *G01N 21/255* (2013.01); *G01B 11/272* (2013.01); *G01J 3/46* (2013.01); *G01N 21/251* (2013.01); *G01N 21/84* (2013.01)

(58) Field of Classification Search
CPC ..... G01N 21/25; G01N 21/255; G01B 11/26; G01B 11/27; G01B 11/272; G01J 3/46
See application file for complete search history.

(56) References Cited

U.S. PATENT DOCUMENTS

| | | | | |
|---|---|---|---|---|
| 4,329,591 | A * | 5/1982 | Fujiwara | G01N 21/86 250/548 |
| 4,343,991 | A * | 8/1982 | Fujiwara | G01D 5/34723 250/227.11 |
| 2001/0050661 | A1* | 12/2001 | Noda et al. | G09G 3/3413 345/32 |
| 2006/0038996 | A1* | 2/2006 | Kuroiwa et al. | G01J 3/02 356/328 |

* cited by examiner

*Primary Examiner* — Michael A Lyons
*Assistant Examiner* — Violeta A Prieto

(57) ABSTRACT

The present application relates to a colorimeter measurement method and a colorimeter for implementing the method. The method includes the following steps: placing a measured sample on a sample platform; shooting a current image of the sample; determining an intersection angle θ between the sample and a moving direction of the sample platform; adjusting a position of a scanning light spot of a colorimeter according to the angle θ, so that the sample coincides with the moving direction of the sample platform; using the colorimeter to scan the measured sample. By implementing the colorimeter measurement method and the colorimeter of the present application, the sample can be placed optionally when it is measured. Specially, when a design value of a measured sample is approximately equal to a size of the measuring light spot, much time can be saved and manpower waste is avoided.

10 Claims, 6 Drawing Sheets

COLORIMETER MEASUREMENT METHOD AND COLORIMETER FOR IMPLEMENTING THE METHOD

FIELD OF THE INVENTION

The present application relates to the field of colorimeters, and more particularly, relates to a colorimeter measurement method and a colorimeter for implementing the method.

BACKGROUND

A multi channel photo detector (MCPD) is a widely used chroma measurement apparatus. A spectroscope of the MCPD can divide light passing through a sample by a full wavelength (380 nm-780 nm) using concave tortuous grids, and the MCPD can transform divided light with various wavelengths into a number of current signals using an optoelectronic array, calculate light spectrum according to the current signals, and finally display the calculated light spectrum.

In a measurement process using the MCPD, a measured sample is fixedly mounted on a platform, and the platform is moved so that the MCPD scans and measures the sample. For example, in the TFT-LCD industry, the MCPD is mainly used to measure red, green, and blue (hereinafter referred to as "RGB") color resists of color filters. In order to measure the RGB color resists simultaneously, the RGB color resists should be horizontally arranged side by side. Since a width of a measuring light spot is generally about 40 μm, if sizes of the RGB color resists of the sample are small, an arranging direction of pixels of the sample should be perpendicular to a top side and a bottom side of a charge-coupled device (CCD) of the MCPD. Otherwise, the measuring light spot may be unable to entirely irradiate the color resists, the measurement data may be wrong, and judgment and evaluation of material properties of the sample may be adversely affected, which may result in that characteristics of products cannot meet requirements. As shown in FIG. 1 and FIG. 2, when such a colorimeter (i.e., an MCPD) is used to scan a conventional color filter 200, the color filer 200 is placed at a predetermined position. A width of a scanning light spot 300 of the colorimeter is generally about 40 μm and slightly less than widths of color resists 201, 202, 203 of the color filter 200. When the color filter 200 is placed correctly, as shown in FIG. 1, the colorimeter is driven according to predetermined step positions, the color resists 201, 202, 203 are irradiated by the scanning light spot 300 in turn, and the scanning light spot 300 does not irradiate any other portion of the color filter 200. However, if the color filter 200 is not placed at the predetermined position precisely, as shown in FIG. 2, and the colorimeter is still driven according to predetermined step positions, the scanning light spot 300 may partially irradiate out of the color resists 201, 202, 203 and result in measurement errors.

SUMMARY

The objective of the present application is to solve this technical problem: aiming at the defect in the prior art that a sample such as a color filter needs to be manually placed at a correct position for being measured normally when the sample is measured by a conventional colorimeter, a colorimeter measurement method and a colorimeter for implementing the method, which can normally measure samples placed optionally, are provided.

A technical solution of the present application configured to solve the aforementioned technical problem is to provide a colorimeter measurement method, which comprises the following steps:

S1, placing a measured sample on a sample platform;

S2, shooting a current image of the sample;

S3, calculating a placement angle deviation θ of the sample according to a measurement sequence of the sample and a moving direction of the sample platform;

S4, adjusting a position of a scanning light spot of a colorimeter according to the placement angle deviation θ;

S5, using the colorimeter to scan the measured sample.

In the colorimeter measurement method of the present application, the measured sample is a color filter.

In the colorimeter measurement method of the present application, the step S3 includes:

S31, selecting a color resist in the color filter, selecting two points at a long side of the color resist, and using the two points to determine a first straight line;

S32, according to the measurement sequence of the sample, drawing a second straight line that is perpendicular to the first straight line;

S33, determining an intersection angle between the second straight line and the moving direction of the sample platform as the placement angle deviation θ.

In the colorimeter measurement method of the present application, the step S4 includes:

embedding a rotating platform that is rotatable in a plane where the sample platform is positioned in the sample platform, fixedly connecting a rotating axle to a center of a bottom of the rotating platform, and driving the rotating platform to rotate in the plane where the sample platform is positioned using the rotating axle.

In the colorimeter measurement method of the present application, the step S4 includes:

embedding a rotating platform that is rotatable in a plane where the sample platform is positioned in the sample platform, providing a transmission wheel being in tight contact with the rotating platform, and driving the rotating platform to rotate in the plane where the sample platform is positioned using friction transmission provided by the transmission wheel.

The present application further provides a colorimeter configured to implement the aforementioned colorimeter measurement method. The colorimeter comprises:

a sample platform configured to place a measured sample; and a scanning lens and a camera spacedly mounted above the sample platform;

wherein, when the camera shoots the measured sample, the colorimeter calculates a placement angle deviation θ of the sample according to a measurement sequence of the sample and a moving direction of the sample platform; the sample platform adjusts a position of a scanning light spot of the colorimeter according to the angle deviation θ; and the scanning lens scans and measures the sample.

In the colorimeter of the present application, the measured sample is a color filter.

In the colorimeter of the present application, the color filter includes a plurality of color resists; one color resist of the color filter is selected, and two points are selected at a long side of the color resist to determine a first straight line; a second straight line that is perpendicular to the first straight line is drawn according to the measurement sequence of the sample; and an intersection angle between the second straight line and the moving direction of the sample platform is determined as the angle deviation θ.

The colorimeter of the present application further comprises:

a rotating platform embedded in the sample platform and being rotatable in a plane where the sample platform is positioned; and a rotating axle fixedly connected to a center of a bottom of the rotating platform;

wherein, the rotating axle drives the rotating platform to rotate in the plane where the sample platform is positioned.

The colorimeter of the present application further comprises:

a rotating platform embedded in the sample platform and being rotatable in a plane where the sample platform is positioned; and a transmission wheel being in tight contact with the rotating platform;

wherein, friction transmission provided by the transmission wheel drives the rotating platform to rotate in the plane where the sample platform is positioned.

By implementing the colorimeter measurement method and the colorimeter for implementing the method of the present application, the following advantages can be achieved: when the sample is measured, the sample can be placed optionally. Specially, when a design value of a measured sample is approximately equal to a size of the measuring light spot, much time can be saved and manpower waste is avoided.

DETAILED DESCRIPTION

Figure 1:
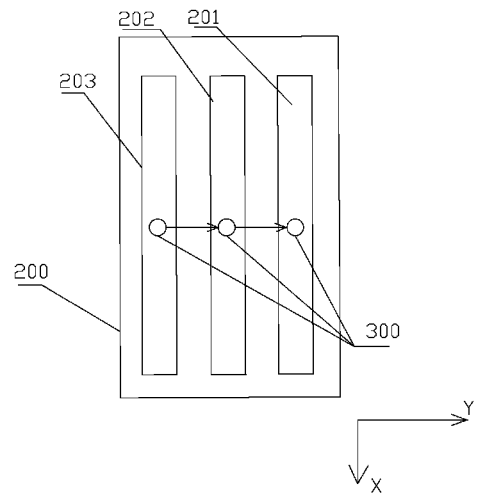
FIG. 1 is a schematic view of scanning a correctly placed color filter according to the prior art.
Figure 2:
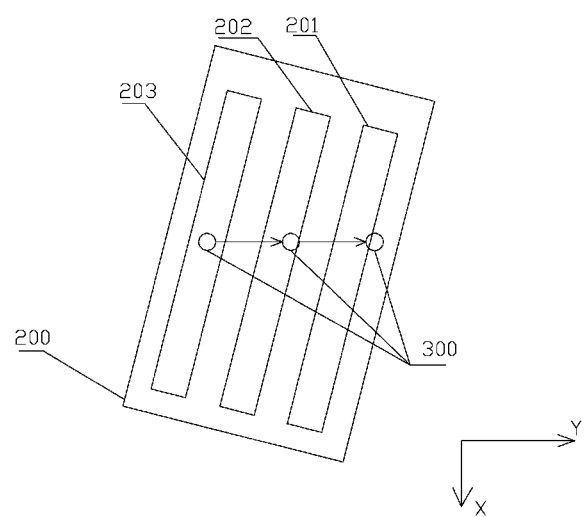
FIG. 2 is a schematic view of scanning an incorrectly placed color filter according to the prior art.

In order to understand the technical features, purpose and the effect of the present invention more clearly, the preferred specific embodiments of the present invention will be described referring to the drawings.

For overcoming the defect in the prior art that a measured sample needs to be placed correctly, and thus much manpower and resource is consumed and measurement error rate is high, in the present application, a placement angle of a sample is analyzed before the sample is scanned and measured. After the placement angle is analyzed, the sample can be adjusted so that a scanning light spot can always irradiate correct positions in formal scanning and measuring processes, and thus accurate measurement can be realized.

Figure 3:
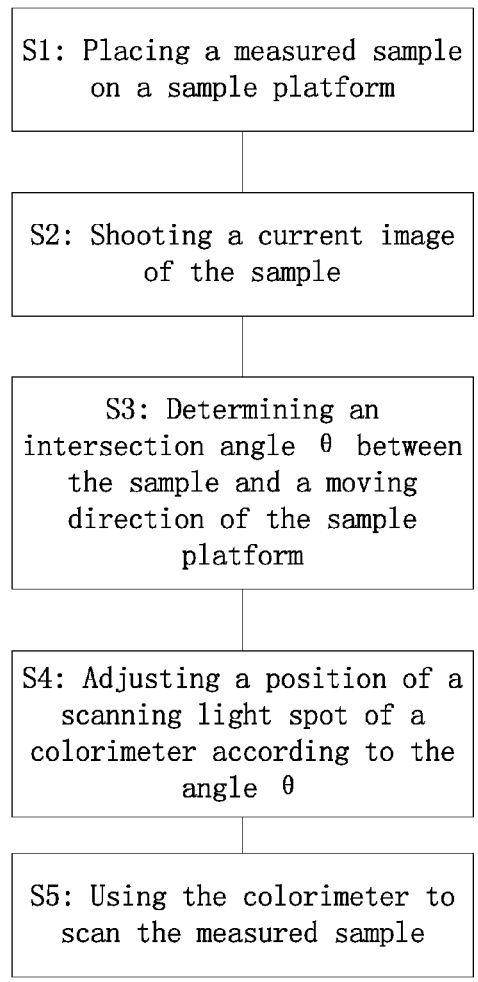
FIG. 3 is a flow chart of a colorimeter measurement method of the present application.

In order to measure samples placed in different postures and positions using a colorimeter, one preferred embodiment of the present application provides a colorimeter measurement method, and FIG. 3 is a flow chart of the method. The method includes the following steps: at first, in a step S1, a measured sample is placed onto a sample platform. In this embodiment, the measured sample is a color filter. A colorimeter is used to scan and measure color resists of the color filter and thereby determine quality of the color resistor. In the measurement process, each color resist of the color filter should be moved into a scanning light spot of the colorimeter to be measured in turn.

After the measured color filter is fixed on the sample platform, a step S2 is executed. In the step S2, a current image of the sample is shot by a camera. In this embodiment, the image of the color filter shot by the camera will be transmitted to a computer system to be analyzed, so that a current placement position of the color filter is determined.

Figure 4:
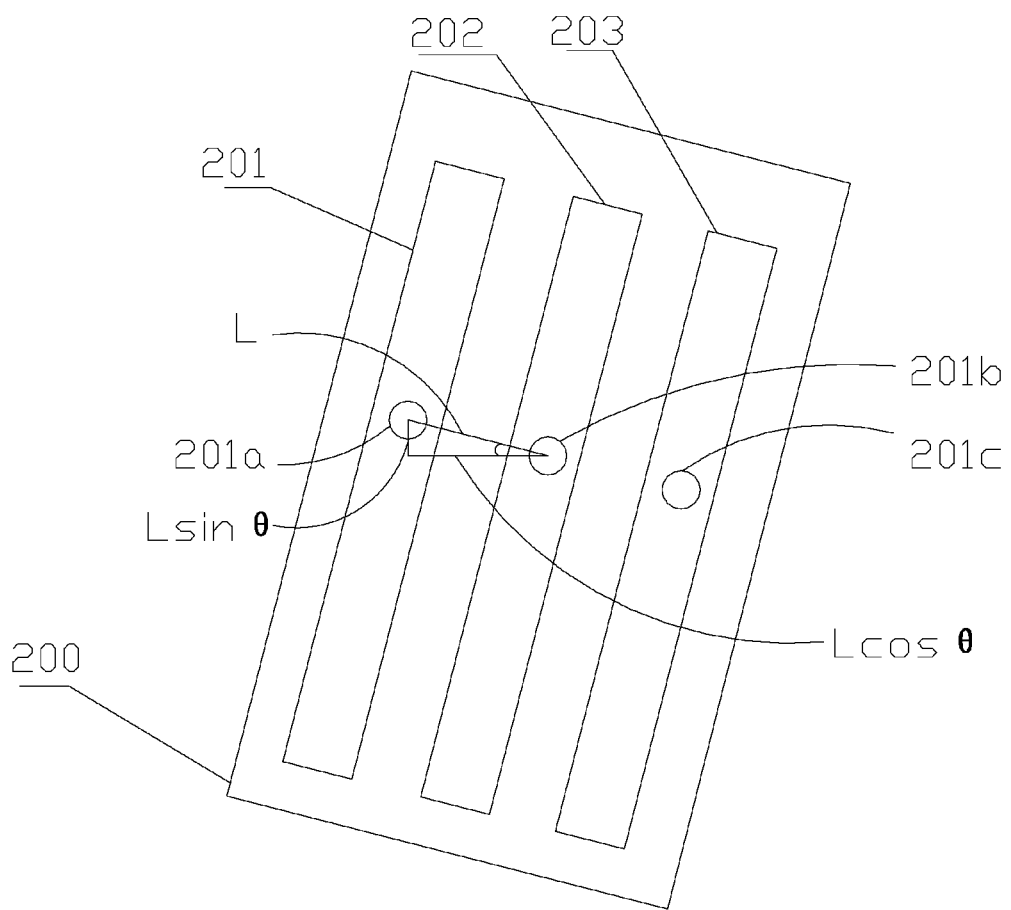
FIG. 4 is a schematic view of using a colorimeter to scan a color filter placed optionally, according to a first embodiment of the colorimeter measurement method of the present application.

Specifically, in a step S3, an intersection angle $\theta$ between the sample and a moving direction of the sample platform. In a step S4, according to the angle $\theta$, the operation for moving the sample to a predetermined position is decomposed into two movements along two directions, so that the scanning light spot can be moved to a correct position relative to the sample. As shown in FIG. 4, a color filter is placed optionally. In this embodiment, it is assumed that a scanning light spot scans color resists of a correctly placed color filter according to a sequence of 201a, 202a, 203a. If the correctly placed color filter needs to move a distance L so that the scanning light spot is moved from one color resist to a next color resist, when the image of the color filter is respectively rotated to an X axis and a Y axis of the movement of the sample platform, two displacement components $L \sin \theta$ and $L \cos \theta$ can be obtained. That is, if a color filter is optionally placed on a sample platform that can move in two-dimensional directions, so long as the sample platform is driven to move a distance $L \sin \theta$ along one direction and move a distance $L \cos \theta$ along another direction, measurement effect of the optionally placed color filter can be the same as measurement effect of a correctly placed color filter. Hardware of the sample platform does not need to be improved, and only a driving displacement of a stepper motor of the sample platform needs to be adjusted.

Finally, in a step S5, the colorimeter drives the sample platform to move along two directions respectively according to the two step sizes $L \sin \theta$ and $L \cos \theta$, and scans the measured sample.

By implementing the aforementioned measurement process, when an operator places a measured color filter, he/she can place the color filter with an optional placement angle. Thus, time consumption of conventional placing methods is obviously reduced.

In the aforementioned embodiment, the optionally placed color filter is driven to move along two directions respectively. In a second embodiment of the present application, the color filter is operated by another method.

The second embodiment includes steps S1 and S2, which are the same as corresponding steps of the first embodiment. According to the steps S1 and S2, a current image of a placed color filter is obtained. Afterwards, the step S3 is executed. In this embodiment, the angle θ is determined by the following method: one of color resists of the color filter is optionally selected, and two points are selected at a long side of the selected color resist to determine a first straight line L1. A second straight line L2, which is perpendicular to the first straight line L1, is drawn in a plane where the color filter is positioned, that is, the second straight line L2 is parallel to two short sides of the selected color resist. According to a measurement sequence of the RGB color resists, a moving direction of the sample platform is determined along the extending direction of the second straight line L2. Finally, an intersection angle formed between the second straight line L2 and the moving direction of the sample platform is considered as the angle θ.

It should be noted that there are generally four placing methods for optionally placing the color filter on the sample platform. The four placing methods are shown in FIGS. 5 to 8 respectively.

Figure 5:
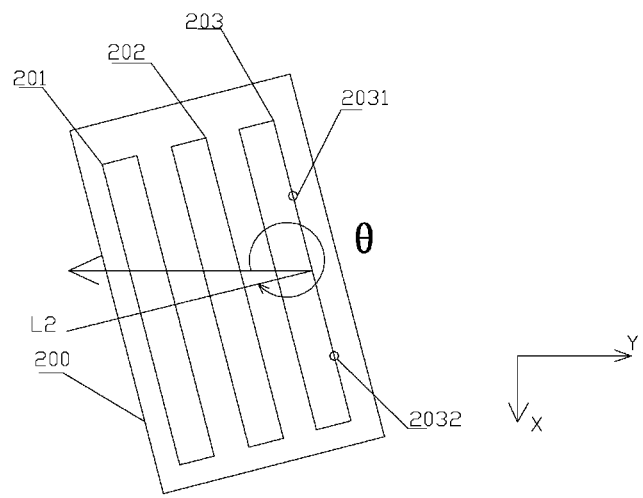
FIG. 5 is a first schematic view of scanning a color filter placed optionally, according to a second embodiment of the colorimeter measurement method of the present application.

As shown in FIG. 5, it is assumed that a current moving direction of the sample platform is the negative direction of the Y axis, and the scanning sequence is a red color resist 201, a green color resist 202, and a blue color resist 203. At first, two points are selected at a long side of any one of the three color resists. In this embodiment, a first point 2031 and a second point 2032 are selected at a long side of the blue color resist 203, and the two points are connected to each other to determine the first straight line L1. A perpendicular of the first straight line L1 is drawn, so that the second straight line L2 is obtained. A rotating angle of a clockwise rotation from the moving direction of the sample platform (i.e., the negative direction of the Y axis) to the second straight line L2 is considered as the angle θ. In this embodiment, the color filter needs to be moved by rotating the sample platform, so that the degree of the angle θ is 0.

Figure 6:
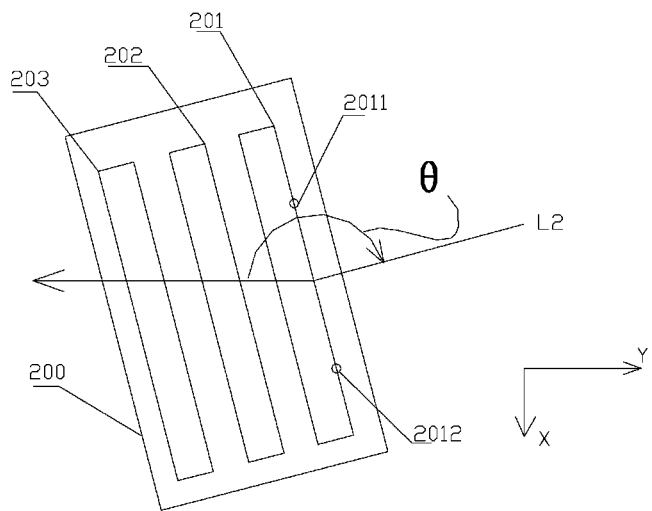
FIG. 6 is a second schematic view of scanning the color filter placed optionally, according to the second embodiment of the colorimeter measurement method of the present application.

It should be noted that a pointing direction of the second straight line L2 should accord with the sequence for scanning the color resists when drawing the second straight line L2. For example, as shown in FIG. 6, a sample platform 100 moves towards the negative direction of the Y axis, and the scanning sequence is the red color resist 201, the green color resist 202, and the blue color resist 203. The straight line L2 should be drawn according to the direction shown in FIG. 5, and the moving direction of the sample platform is clockwise rotated to the second straight line L2 to form the angle θ.

Figure 7:
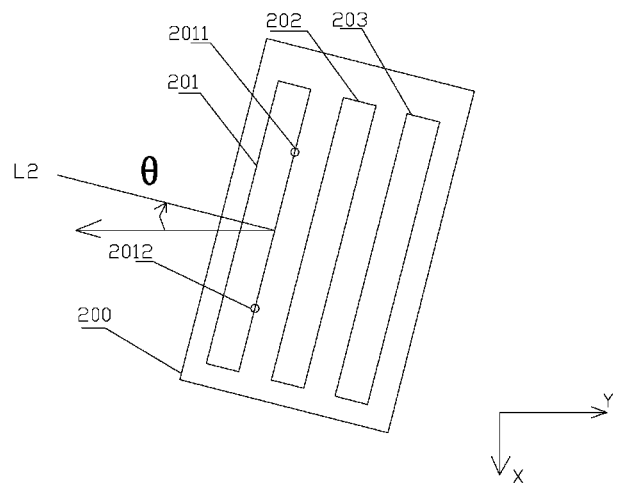
FIG. 7 is a third schematic view of scanning the color filter placed optionally, according to the second embodiment of the colorimeter measurement method of the present application.
Figure 8:
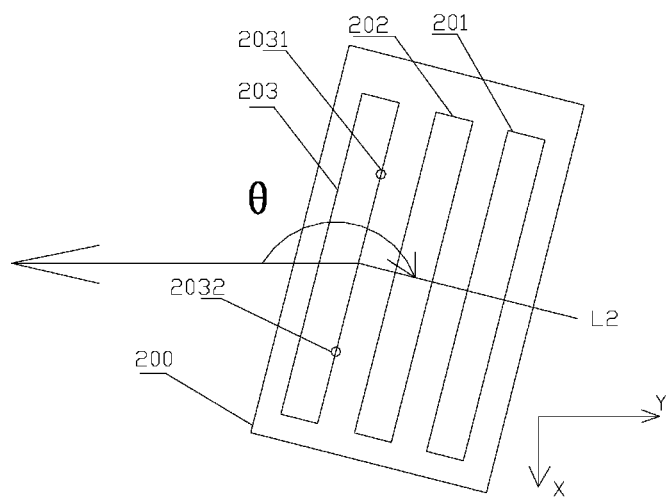
FIG. 8 is a fourth schematic view of scanning the color filter placed optionally, according to the second embodiment of the colorimeter measurement method of the present application.

An optionally placed color filter 200 can also be placed according to situations shown in FIG. 7 and FIG. 8. In embodiments shown in FIG. 7 and FIG. 8, methods for determining the intersection angle θ between the color filter 200 and a moving direction of the sample platform are the same as that of the embodiments shown in FIG. 5 and FIG. 6: at first, the moving direction of the sample platform and the sequence for scanning the color resists are determined; a long side of any one of the color resist is optionally selected, two points are selected at the long side, and the two points are connected to each other to determine the first straight line L1; afterwards, the second straight line L2 that is perpendicular to the first straight line L1 is drawn. When drawing the second straight line L2, it should be ensured that the extending second straight line L2 passes through the color resists according to a sequence that is the same as a predetermined sequence for scanning the color resists. Finally, the moving direction of the sample platform is clockwise rotated to the second straight line L2 to form the angle θ.

After the intersection angle θ between the placed color filter and the moving direction of the sample platform is determined, in the step S4, the sample platform is rotated at the angle θ, so that the sample coincides with the moving direction of the sample platform. That is, the angle θ is adjusted to be 0 after the rotation. It should be understood by one of ordinary skill in the art that, as shown in FIG. 5 and FIG. 8, if the angle θ is more than 180 degrees, the angle θ can be adjusted to be 360 degrees by rotation. In the placing effect, 360 degrees is equivalent to θ.

When the step S4 is completed, the measured color filter is rotated to a correct placed position, and thus the step S5 can be executed. A scanning lens of the colorimeter scans the color resists of the color filter. The sample platform is driven by a stepper motor to move the color resists of the color filter into a scanning light spot of the scanning lens in turn, so that the color resists are scanned.

Figure 9:
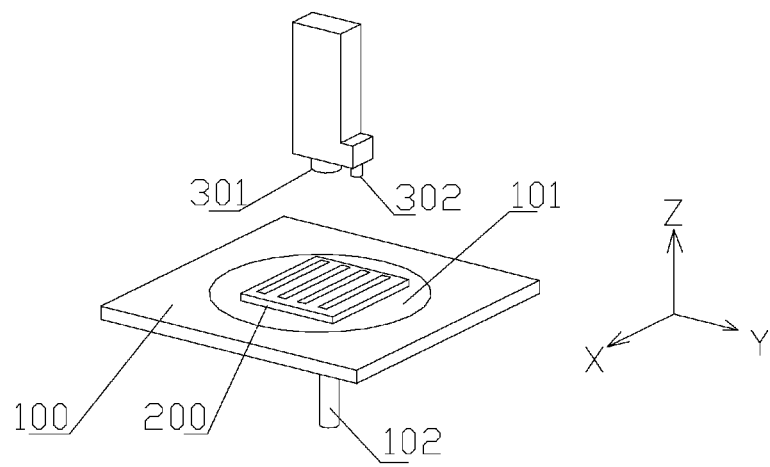
FIG. 9 is a structural schematic view of a first embodiment of a colorimeter of the present application.

The present application further provided a colorimeter for executing the measurement process of the second embodiment. FIG. 9 is a structural schematic view of the colorimeter. The colorimeter includes a sample platform 100 configured to place measured samples, and a rotating platform 101, which is rotatable in a plane where the sample platform 100 is positioned, is embedded in a center of the sample platform 100. The sample platform 100 further includes a rotating axle 102 configured to drive the rotating platform 101 to rotate. One end of the rotating axle 102 is fixedly connected to a center of a bottom surface of the rotating platform 101, and the other end of the rotating axle 102 is connected to a conventional stepper motor (not shown). When the rotating axle 102 is assembled completely, the stepper motor can drives the rotating axle 102 and the sample platform 100 to steppingly move along a horizontal direction.

A scanning lens 301 and a camera 302 are mounted above a top surface of the rotating platform 101. Preferably, the scanning lens 301 and a camera 302 are closely juxtaposed. Both a scanning area of the scanning lens 301 and a shooting area of the camera 302 are aligned with the top surface of the rotating platform 101. Wherein, the scanning lens 301 is used to scan and measure color resists of color filters, and the camera 302 is used to shoot measured samples placed on the rotating platform 101. In this embodiment, the scanning lens 301 and the camera 302 are closely juxtaposed to save assembly space. However, the present application does not limit specific positions of the two components, so long as the scanning lens 301 can normally scan the color resists of the color filters and the camera 302 can normally shoot the measured color filters.

In a measurement process using the aforementioned colorimeter, a measured sample, such as a color filter 200, is fixed on the top surface of the rotating platform 101. The color filter 200 can be placed optionally, and short sides of the color resists of the color filter 200 do not need to be parallel to a stepping direction of the sample platform 100.

When the color filter 200 is placed and fixed, the camera 302 shoots a current image of the color filter 200. The image shot by the camera 302 is transmitted to a conventional computer system (not shown) to be analyzed, so that a current position for placing the color filter 200 is determined. The computer system further analyzes the image to obtain the intersection angle θ between the current position for placing color filter 200 and a steppingly moving direction of the sample platform 100. Afterwards, the computer system controls the rotating axle 102 to rotate at the angle θ, and the rotating axle 102 further drives the rotating platform 101 to rotate. By the rotation operation, an angle deviation of the optionally placed color filter 200 can be compensated.

When the angular rotation of the rotating platform 101 is completed, the stepper motor moves the sample platform 100, so that a scanning light spot of the scanning lens 301 is aligned with the color resists of the color filter 200. Afterwards, the scanning lens 301 scans and measures the color resists. When scan and measurement of one color resist are completed, the stepper motor drives the sample platform 100 to move, so that a next color resist is moved into the scanning light spot of the scanning lens 301 to be scanned and measured. When all of the color resists are scanned, measurement for the color filter 200 is completed.

In the colorimeter embodiment shown in FIG. 9, the rotating axle 102 is fixed on the center of the bottom surface of the rotating platform 101 to rotate the color filter 200. It should be understood by one of ordinary skill in the art that the color filter 200 can also be rotated by other methods. For example, in a colorimeter shown in FIG. 10, the rotating platform 101 is rotated by another method.

Figure 10:
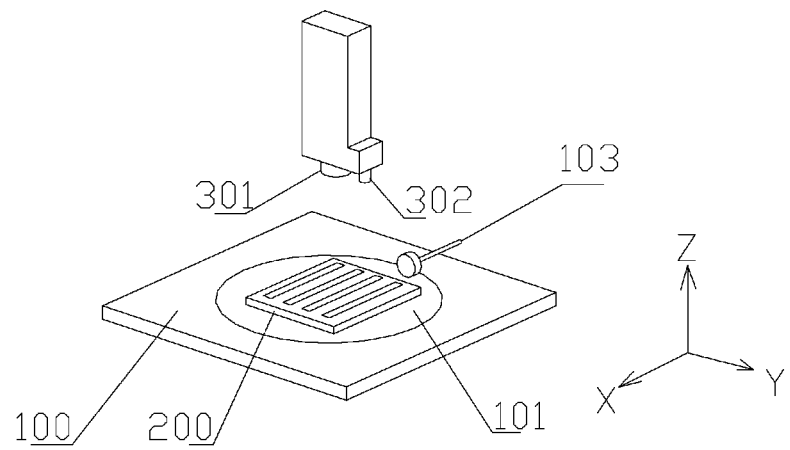
FIG. 10 is a structural schematic view of a second embodiment of a colorimeter of the present application.

The colorimeter shown in FIG. 10 includes a sample platform 100 configured to place measured samples, and a rotating platform 101, which is rotatable in a plane where the sample platform 100 is positioned, is embedded in a center of the sample platform 100. This embodiment differs from the aforementioned embodiment in that this embodiment does not use the rotating axle 102 fixedly connected to the bottom of the rotating platform 101. In this embodiment, a transmission wheel 103 is mounted on the top of the rotating platform 101 and positioned near the periphery of the rotating platform 101. The transmission wheel 103 is in tight contact with the rotating platform 101, so that the transmission wheel 103 can drive the rotating platform 101 because of friction. When the transmission wheel 103 rotates around a central axis of itself, the rotating platform 101 can be driven to rotate in the plane where the sample platform 100 is positioned by friction.

When the transmission wheel 103 drives the rotating platform 101 to rotate to a correct position, the transmission wheel 103 is slightly raised, so that the transmission wheel 103 does not contact the rotating platform 101. The stepper motor drives the sample platform 100 to move, so that the scanning light spot of the scanning lens 301 is aligned with one of the color resists of the color filter 200. Afterwards, the scanning lens 301 scans and measures the color resist. When scan and measurement of the color resist are completed, the stepper motor drives the sample platform 100 to move, so that a next color resist is moved into the scanning light spot of the scanning lens 301 to be scanned and measured. When all of the color resists are scanned, measurement for the color filter 200 is completed.

Furthermore, the transmission wheel 103 can also be replaced by a transmission gear. Correspondingly, a ring rack can be mounted on the periphery of the top surface of the rotating platform 101. The transmission gear engages the ring rack, and the rotating platform 101 is driven to rotate by gear drive.

In the aforementioned embodiments, the color filter 200 is used as the measured sample to describe the present application. However, the specific use of the present application is not limited here. When a samples having other structures is measured, the rotating angle θ can be determined according to specific structural features of the sample, and the sample can be rotated to adjust the angle θ to be 0.

In these embodiments of the present application, the placement angles of the measured samples are analyzed before the actual measurement processes, and the measured samples are moved to correct positions by rotations. In this way, the positions of the samples do not need to be manually adjusted in the measurement processes.

While the present invention has been described with the drawings to preferred embodiments which is merely a hint rather than a limit, it will be understood by those skilled in the art that various changes may be made and equivalents may be substituted without departing from the scope of the present invention. But all the changes will be included within the scope of the appended claims.

What is claimed is:

1. A colorimeter measurement method, comprising the following steps:
   S1, placing a measured sample on a sample platform;
   S2, shooting a current image of the sample;
   S3, calculating a placement angle deviation θ of the sample according to a measurement sequence of the sample and a moving direction of the sample platform;
   S4, adjusting a position of a scanning light spot of a colorimeter according to the placement angle deviation θ;
   S5, using the colorimeter to scan the measured sample.

2. The colorimeter measurement method according to claim 1, wherein, the measured sample is a color filter.

3. The colorimeter measurement method according to claim 2, wherein, the step S3 includes:
   S31, selecting a color resist in the color filter, selecting two points at a long side of the color resist, and using the two points to determine a first straight line;
   S32, according to the measurement sequence of the sample, drawing a second straight line that is perpendicular to the first straight line;
   S33, determining an intersection angle between the second straight line and the moving direction of the sample platform as the placement angle deviation θ.

4. The colorimeter measurement method according to claim 1, wherein, the step S4 includes:
   embedding a rotating platform that is rotatable in a plane where the sample platform is positioned in the sample platform, fixedly connecting a rotating axle to a center of a bottom of the rotating platform, and driving the rotating platform to rotate in the plane where the sample platform is positioned using the rotating axle.

5. The colorimeter measurement method according to claim 1, wherein, the step S4 includes:
   embedding a rotating platform that is rotatable in a plane where the sample platform is positioned in the sample platform, providing a transmission wheel being in tight contact with the rotating platform, and driving the rotating platform to rotate in the plane where the sample platform is positioned using friction transmission provided by the transmission wheel.

6. A colorimeter, comprising:
   a sample platform configured to place a measured sample; and
   a scanning lens and a camera spacedly mounted above the sample platform;
   wherein, when the camera shoots the measured sample, the colorimeter calculates a placement angle deviation θ of the sample according to a measurement sequence of the sample and a moving direction of the sample platform; the sample platform adjusts a position of a scanning light spot of the colorimeter according to the angle deviation θ; and the scanning lens scans and measures the sample.

7. The colorimeter according to claim 6, wherein, the measured sample is a color filter.

8. The colorimeter according to claim 7, wherein, the color filter includes a plurality of color resists; one color resist of the color filter is selected, and two points are selected at a long side of the color resist to determine a first straight line; a second straight line that is perpendicular to the first straight line is drawn according to the measurement sequence of the sample; and an intersection angle between the second straight line and the moving direction of the sample platform is determined as the angle deviation θ.

9. The colorimeter according to claim 6, further comprising:
- a rotating platform embedded in the sample platform and being rotatable in a plane where the sample platform is positioned; and
- a rotating axle fixedly connected to a center of a bottom of the rotating platform;
- wherein, the rotating axle drives the rotating platform to rotate in the plane where the sample platform is positioned.

10. The colorimeter according to claim 6, further comprising:
- a rotating platform embedded in the sample platform and being rotatable in a plane where the sample platform is positioned; and
- a transmission wheel being in tight contact with the rotating platform;
- wherein, friction transmission provided by the transmission wheel drives the rotating platform to rotate in the plane where the sample platform is positioned.

* * * * *